United States Patent

Vanney et al.

[11] Patent Number: 6,139,541
[45] Date of Patent: Oct. 31, 2000

[54] GUIDE FOR TRANSMYOCARDIAL IMPLANT

[75] Inventors: Guy P. Vanney, Blaine; Michael L. Krogh, St. Paul, both of Minn.

[73] Assignee: Heartstent Corporation, St. Paul, Minn.

[21] Appl. No.: 09/145,843

[22] Filed: Sep. 2, 1998

[51] Int. Cl.$^7$ .................................................. A61B 17/00
[52] U.S. Cl. ................................ 606/1; 606/108; 623/900
[58] Field of Search ..................... 606/1, 108; 623/900; 604/8

[56] References Cited

U.S. PATENT DOCUMENTS

| 5,429,144 | 7/1995 | Wilk . | |
|---|---|---|---|
| 5,755,682 | 5/1998 | Knudson et al. . | |
| 5,893,848 | 4/1999 | Negus et al. | 606/41 |
| 5,935,141 | 8/1999 | Weldon | 606/167 |
| 5,971,993 | 10/1999 | Hussein et al. | 606/108 |
| 5,976,164 | 11/1999 | Bencini et al. | 606/170 |
| 5,984,956 | 11/1999 | Tweden et al. | 623/1 |

FOREIGN PATENT DOCUMENTS

| 2 316 322 | 2/1998 | United Kingdom . |
|---|---|---|
| WO 98/08456 | 3/1998 | WIPO . |

OTHER PUBLICATIONS

U.S. application No. 08/944,313, entitled Transmyocardial Implant, 17 pages.
U.S. application No. 09/063,160, entitled "Transmyocardial Implant Procedure and Tools", 33 pages.

*Primary Examiner*—Linda C. M. Dvorak
*Assistant Examiner*—Jocelyn Debra Ram
*Attorney, Agent, or Firm*—Merchant & Gould P.C.

[57] ABSTRACT

An apparatus controls a direction of formation of a hole through a myocardium for subsequent placement into the hole of a myocardial portion of a transmyocardial implant. The implant also includes a coronary portion having a coronary axis set at an implant angle to a myocardial axis of the myocardial portion. The apparatus includes a base member having base surface for placement against an epicardial surface of a heart adjacent a coronary vessel having a vessel axis. The base member has a determinable base axis for placement of the base surface on the epicardial surface with the base axis parallel with the vessel axis. A support member supports a myocardial penetrator for movement along a support axis in a line of travel parallel to the support axis and substantially restricting the myocardial penetrator from movement transverse to the support axis. The support member is secure to the base member with the support axis and base axis defining a support angle. The support angle and the implant angle are supplementary angles.

4 Claims, 9 Drawing Sheets

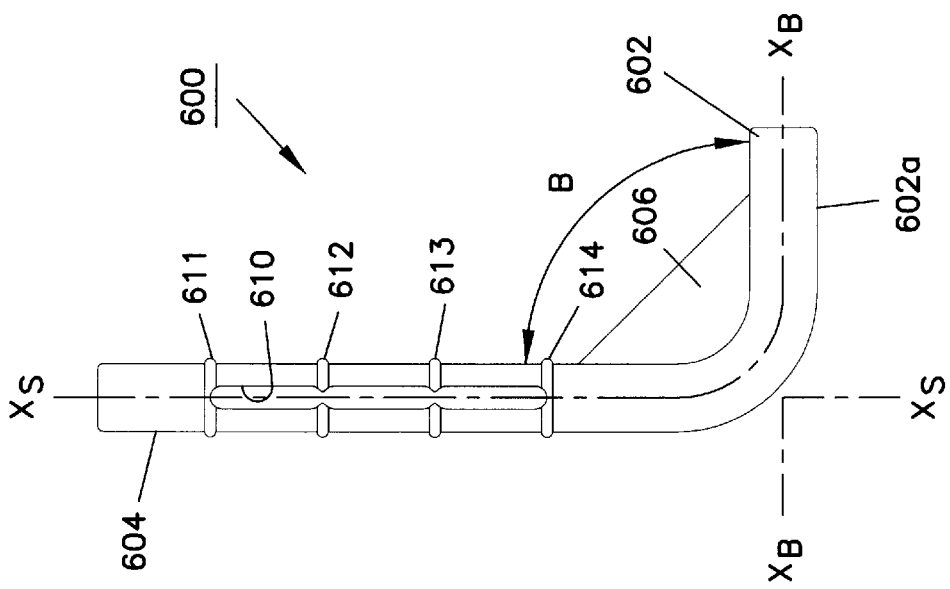
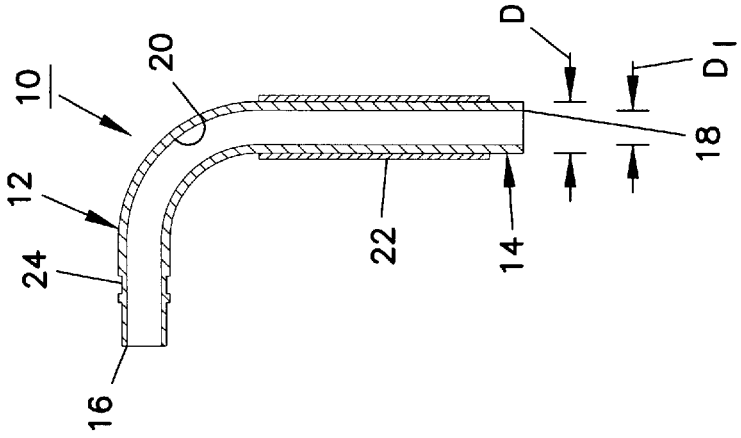
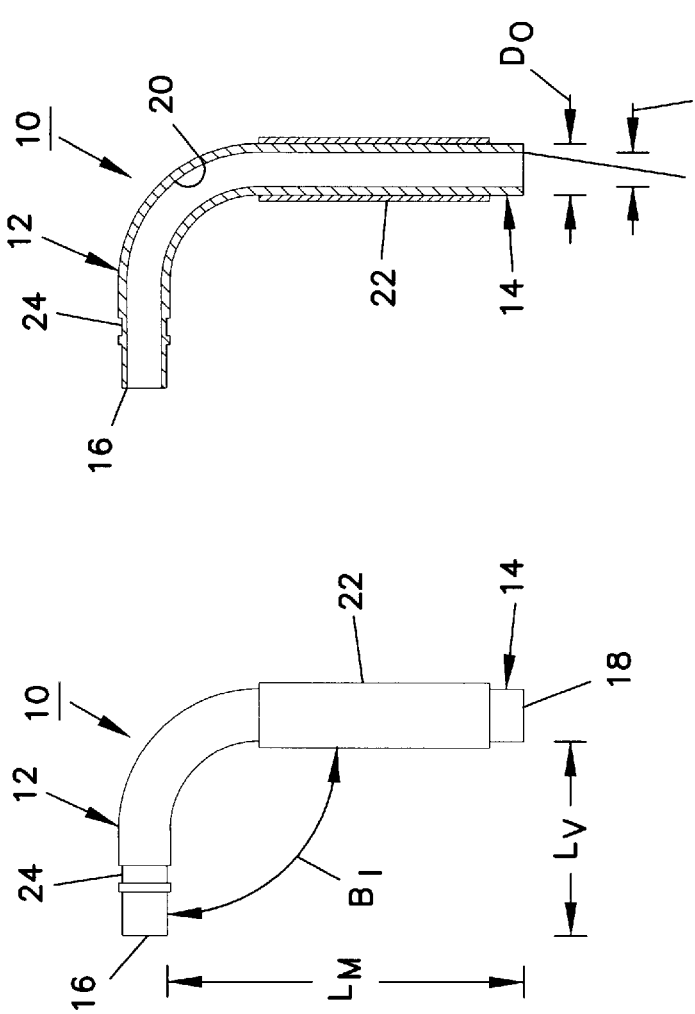

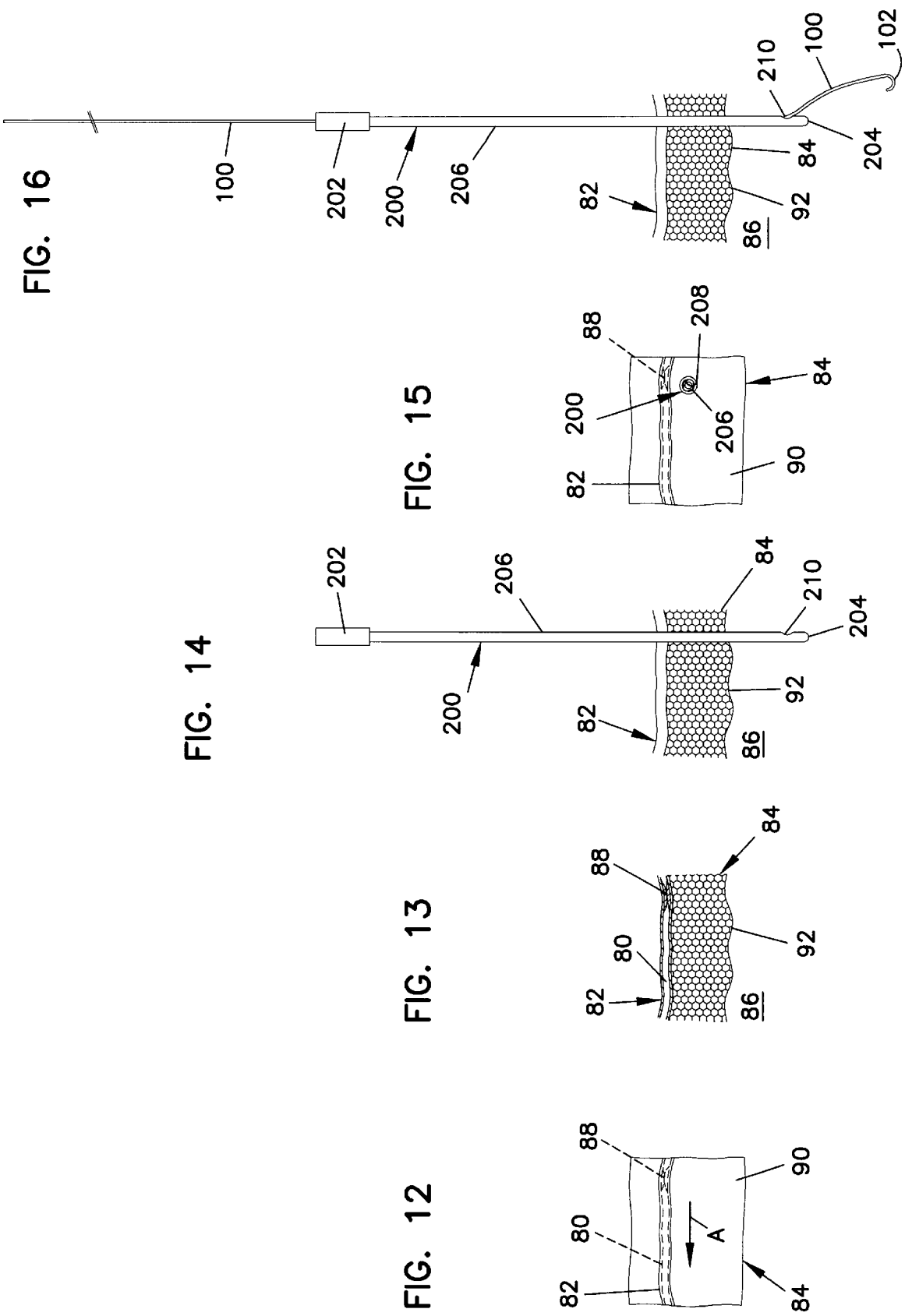

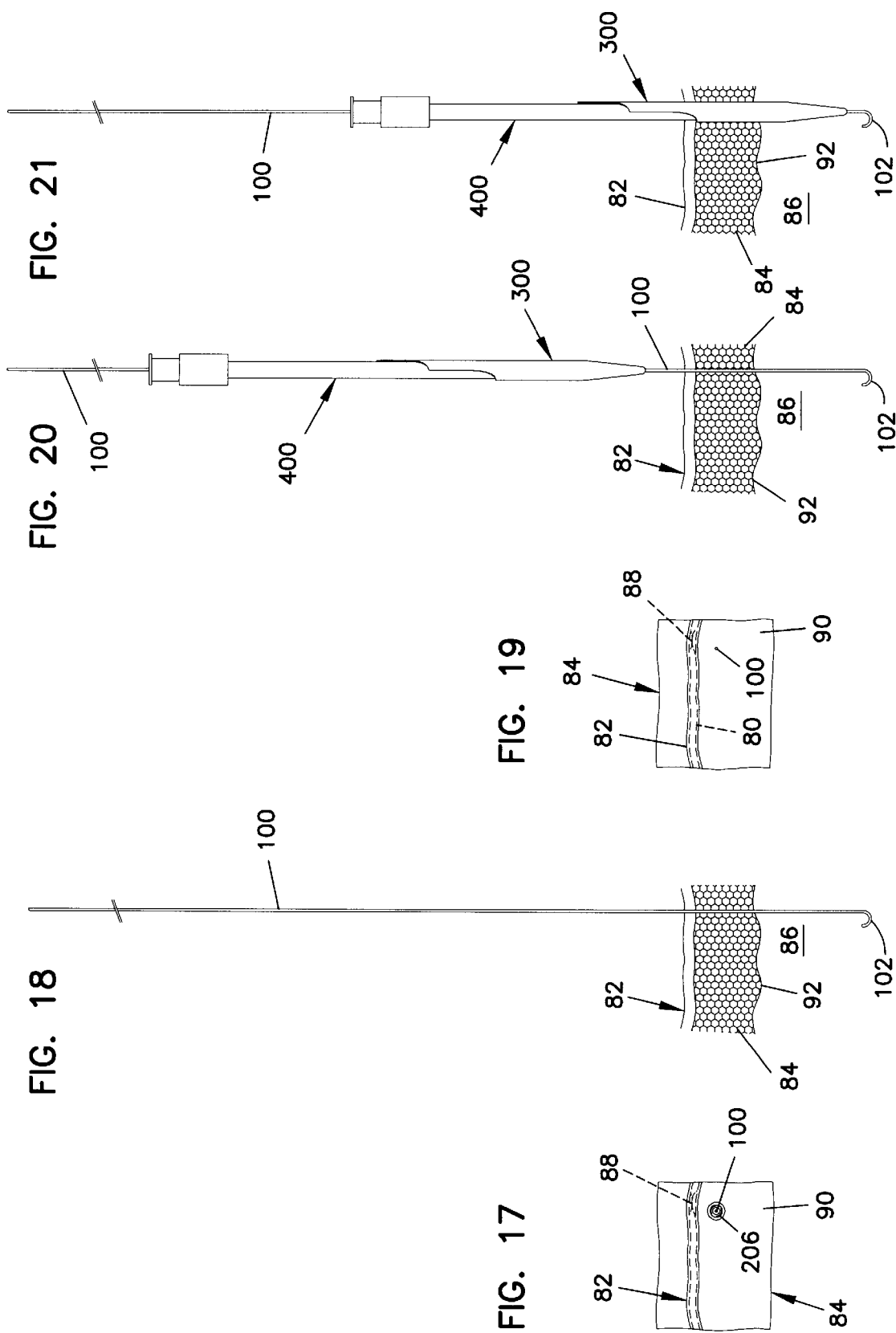

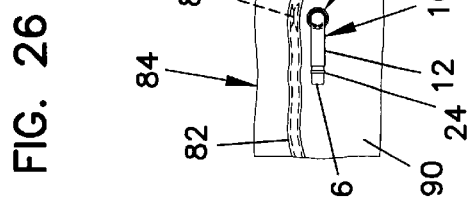
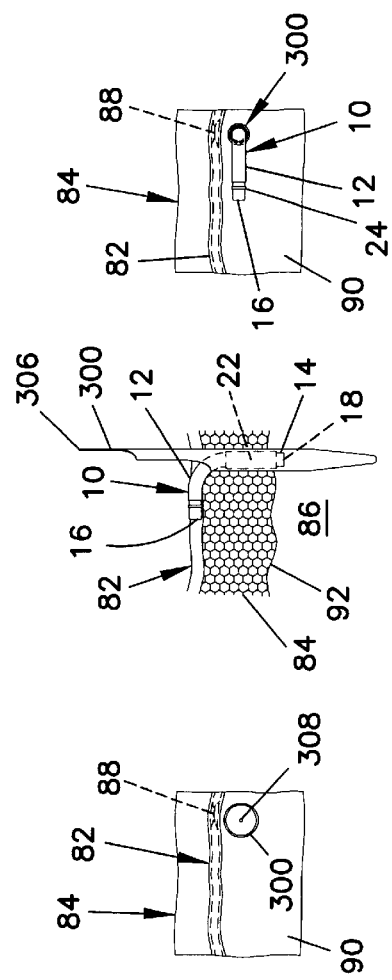
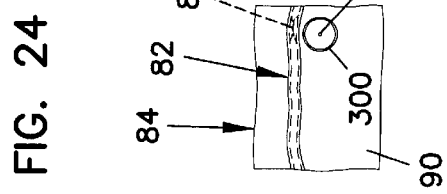
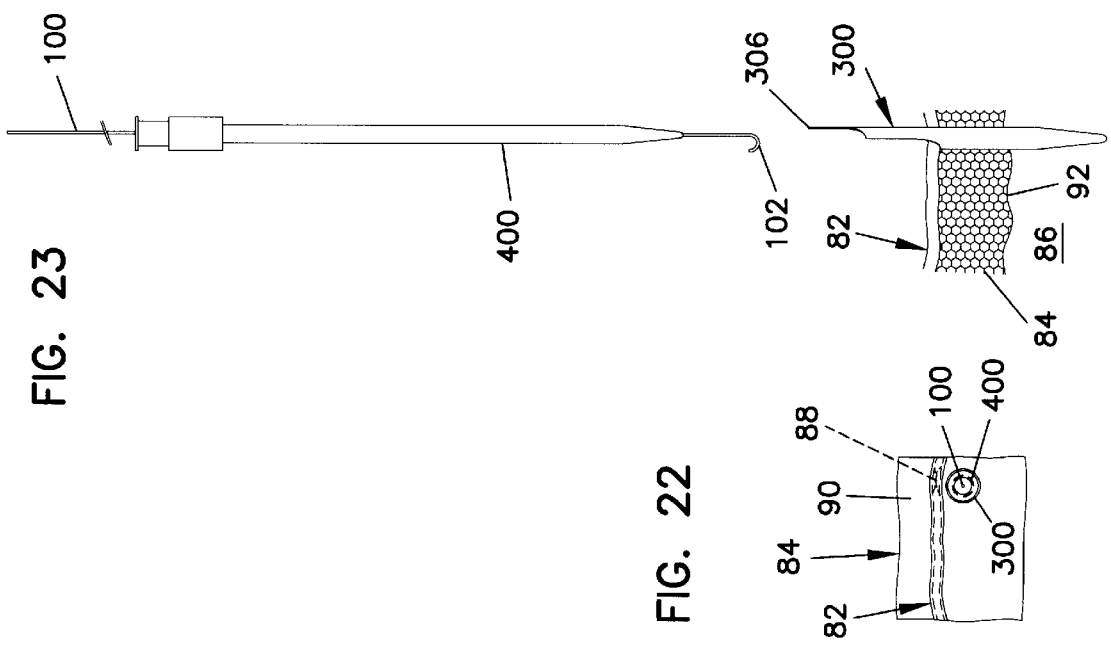

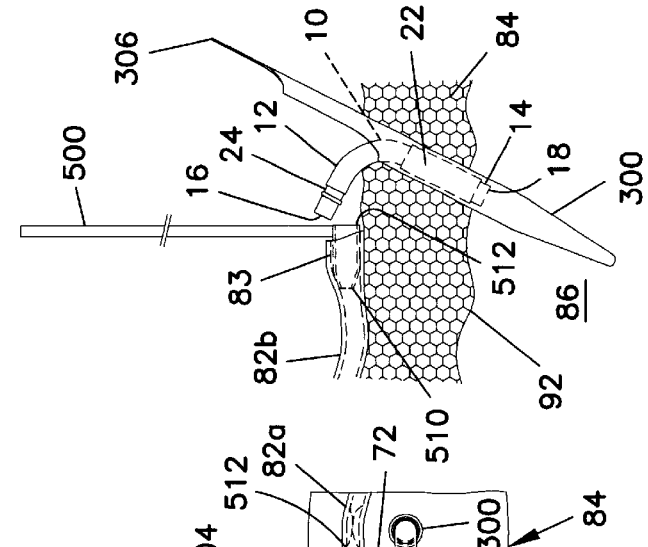
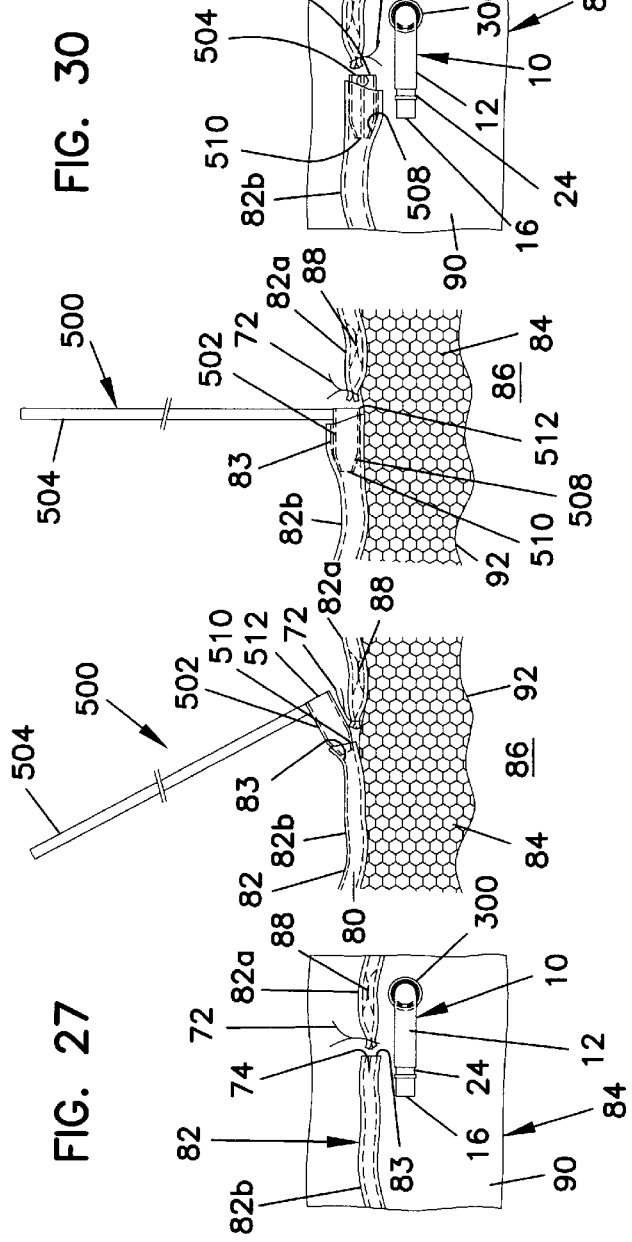

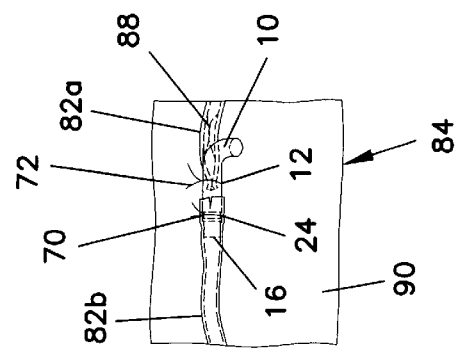
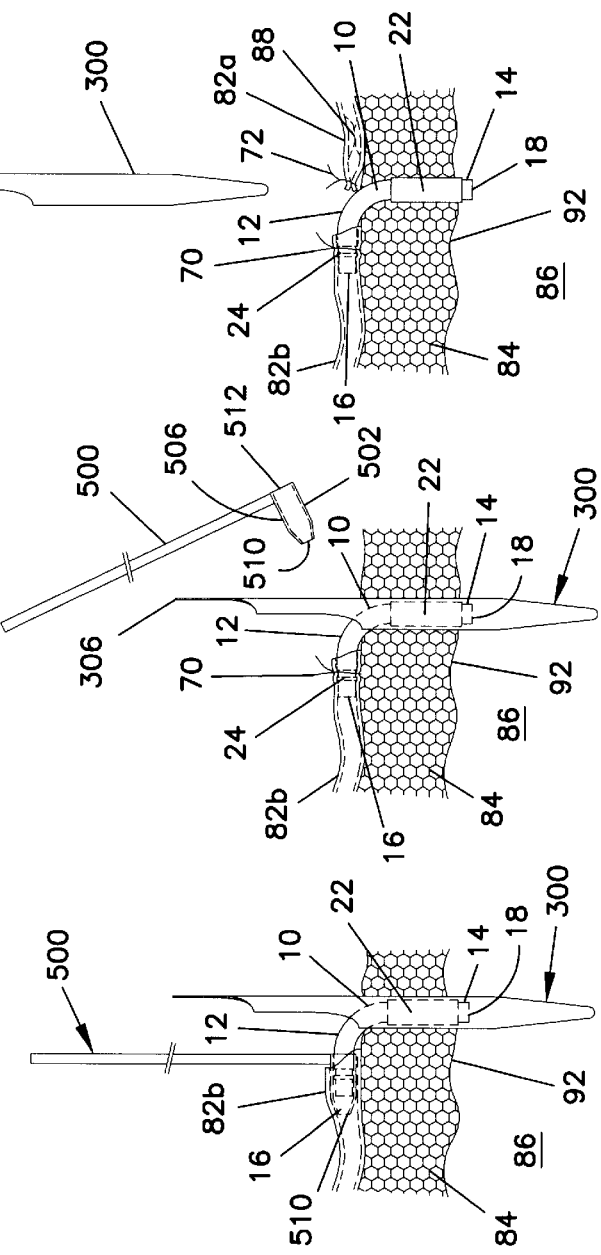

GUIDE FOR TRANSMYOCARDIAL IMPLANT

BACKGROUND OF THE INVENTION

1. Field of the Invention

The present invention pertains to procedures for cardiac revascularization and related tools for forming a blood flow path through a heart wall from a heart chamber to a coronary vessel. More particularly, this invention pertains to a tool to assist in penetrating a heart wall at an angle selected to insure axial alignment of a transmyocardial implant within a coronary vessel.

2. Description of the Prior Art

Commonly assigned U.S. Pat. No. 5,755,682 dated May 26, 1998 and commonly assigned and co-pending U.S. patent application Ser. No. 08/882,397 filed Jun. 25, 1997, entitled "Method and Apparatus for Performing Coronary Bypass Surgery", and filed in the name of inventors Mark B. Knudson and William L. Giese, teach an implant for defining a blood flow conduit directly from a chamber of the heart to a lumen of a coronary vessel. The text of the '397 application has been published on Feb. 25, 1998 in corresponding UK Patent Application GB 2 316 322 A. An embodiment disclosed in the aforementioned patent and application teaches an L-shaped implant in the form of a rigid conduit. The conduit has one leg sized to be received within a lumen of a coronary artery and a second leg sized to pass through the myocardium and extend into the left ventricle of the heart. As disclosed in the above-referenced patent and application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, entitled "Transmyocardial Implant", and filed in the name of inventors Katherine S. Tweden, Guy P. Vanney and Thomas L. Odland, teaches an implant such as that shown in the aforementioned '682 patent and '397 application with an enhanced fixation structure. One embodiment of the enhanced fixation structure includes a fabric surrounding at least a portion of the conduit to facilitate tissue growth on the exterior of the implant.

Implants such as those shown in the aforementioned patent and applications include a portion to be placed within a coronary vessel and a portion to be placed within the myocardium. When placing an implant in the myocardium, a hole is formed through the heart wall into the left ventricle. Commonly assigned and co-pending U.S. patent application Ser. No. 09/063,160 filed Apr. 20, 1998, entitled "Transmyocardial Implant Procedure and Tools", and filed in the name of inventors Guy P. Vanney, Thomas L. Odland and Eric E. Solien teaches a procedure and related tools for placement of an implant in a myocardium and coronary vessel.

When placing a transmyocardial implant, it is desirable that the implant be axially aligned with a coronary vessel following such implantation. The present invention is directed to a tool for assisting in achieving such alignment.

SUMMARY OF THE INVENTION

According to a preferred embodiment of the present invention, an apparatus is disclosed for controlling a direction of formation of a hole through a myocardium. The hole receives a myocardial portion of a transmyocardial implant. The implant also includes a coronary portion having a coronary axis set at an implant angle to a myocardial axis of the myocardial portion. The apparatus includes a base member having base surface for placement against an epicardial surface of a heart adjacent a coronary vessel having a vessel axis. The base member has a determinable base axis for placement of the base surface on the epicardial surface with the base axis parallel with the vessel axis. A support member supports a myocardial penetrator for movement along a support axis in a line of travel parallel to the support axis and substantially restricting the myocardial penetrator from movement transverse to the support axis. The support member is secure to the base member with the support axis and base axis defining a support angle. The support angle and the implant angle are supplementary angles.

BRIEF DESCRIPTION OF THE DRAWINGS

FIG. 1 is a side elevation view of a transmyocardial implant;

FIG. 2 is a side cross-sectional view of the implant of FIG. 1;

FIG. 3 is a front elevation view of a guide tool according to the present invention;

FIG. 12 is a plan view of an obstructed coronary artery lying on an outer surface of a heart wall;

FIG. 13 is a side sectional view of the coronary artery of FIG. 12 showing the artery, obstruction and a myocardium in cross-section;

FIG. 14 is the view of FIG. 13 following placement of a guide needle with the guide needle not shown in cross-section and with the coronary obstruction not shown for ease of illustration;

FIG. 15 is a top plan view of FIG. 14 (and showing a coronary obstruction) with the guide needle shown in transverse cross-section at the heart wall surface;

FIG. 16 is the view of FIG. 14 following placement of a guide wire through the guide needle;

FIG. 17 is a top plan view of FIG. 16 with the guide wire and guide needle shown in transverse cross-section at the heart wall surface;

FIG. 18 is the view of FIG. 16 following removal of the guide needle;

FIG. 19 is a top plan view of FIG. 18 with the guide wire shown in transverse cross-section at the heart wall surface;

FIG. 20 is the view of FIG. 18 showing placement of the myocardial dilator of FIG. 10 and the myocardial sheath on the guide wire and before insertion of a myocardial dilator and a myocardial sheath through the myocardium;

FIG. 21 is the view of FIG. 20 following placement of the myocardial dilator and myocardial sheath through the myocardium;

FIG. 22 is a top plan view of FIG. 21 with the guide wire, myocardial dilator and myocardial sheath shown in transverse cross-section at the heart wall surface;

FIG. 23 is the view of FIG. 21 showing removal of the myocardial dilator and guide wire and leaving the myocardial sheath in the myocardium;

FIG. 24 is a top plan view of FIG. 23 with the myocardial sheath shown in transverse cross-section at the heart wall surface;

FIG. 25 is the view of FIG. 23 following complete removal of the myocardial dilator and guide wire and following placement of a myocardial portion of the transmyocardial implant of FIG. 1 within the myocardial sheath;

FIG. 26 is a top plan view of FIG. 25 with the myocardial sheath shown in transverse cross-section at the heart wall surface;

FIG. 27 is the view of FIG. 26 following incision of the artery and ligation of the artery distal to the obstruction;

FIG. 28 is a side sectional view of FIG. 27 (without showing the implant and myocardial sheath) showing initial insertion of a coronary vessel sheath into the coronary artery;

FIG. 29 is a side sectional view of FIG. 28 (without showing the implant and myocardial sheath) showing full insertion of the coronary vessel sheath into the coronary artery;

FIG. 30 is a top plan view of FIG. 29 showing the implant and with the myocardial sheath shown in transverse cross-section at the heart wall surface;

FIG. 31 is a side sectional view of FIG. 30 showing the implant and myocardial sheath (not shown in cross section) tilted for placement of a coronary portion of the implant within the coronary vessel sheath and, for ease of illustration, not showing a proximal portion of the artery;

FIG. 32 is the view of FIG. 31 following full placement of the coronary portion of the implant within the coronary vessel sheath;

FIG. 33 is the view of FIG. 32 following suture of the artery to the coronary portion of the implant and showing removal of the coronary vessel sheath;

FIG. 34 is the view of FIG. 33 showing removal of the myocardial sheath;

FIG. 35 is a top plan view of the elements of FIG. 34 following complete removal of the myocardial sheath.

DESCRIPTION OF THE PREFERRED EMBODIMENT

Figure 4:
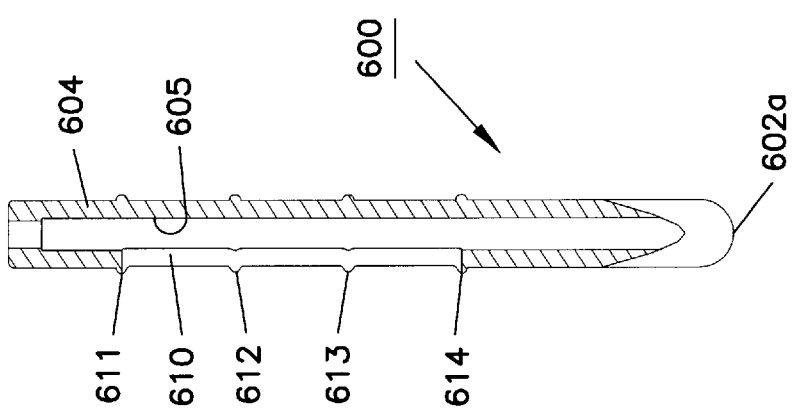
FIG. 4 is a side elevation view of the guide tool of FIG. 3.
Figure 5:
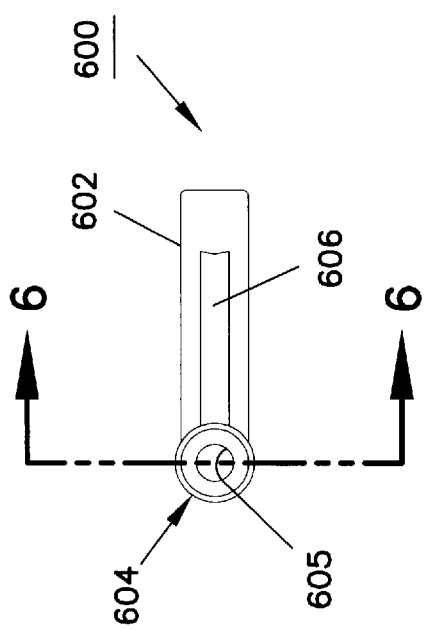
FIG. 5 is a top view of the guide tool of FIG. 3.
Figure 6:
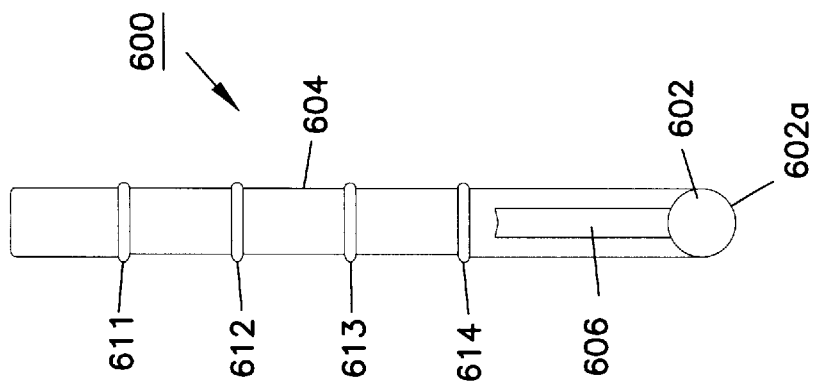
FIG. 6 is a view taken along line 6—6 of FIG. 5.

Referring now to the several drawing figures, in which identical elements are numbered identically throughout, a description of a preferred embodiment of the present invention will now be provided. Throughout the description, specific dimensions and materials of elements of the invention may be given. Such specificity is presented to facilitate an understanding of the invention and is not intended to limit the scope of the claims appended hereto.

Commonly assigned and co-pending U.S. patent application Ser. No. 09/063,160 filed Apr. 20, 1998, (now U.S. Pat. No. 6,029,672) entitled "Transmyocardial Implant Procedure and Tools", and filed in the name of inventors Guy P. Vanney, Thomas L. Odland and Eric E. Solien teaches a procedure and related tools for placement of an implant in a myocardium and coronary vessel.

The implant is a conduit 10 in the form of an L-shaped rigid tube. The conduit 10 may be formed of titanium or other rigid biocompatible material such as pyrolytic carbon or may be titanium coated with pyrolytic carbon or other anti-thrombotic material. The material of the conduit 10 is preferably a rigid material in order to withstand contraction forces of the myocardium 84. By way of example, the implant 10 will have an outside diameter $D_O$ of about 3 millimeters and an internal diameter $D_I$ of about 2 millimeters to provide a wall thickness of about 0.5 millimeters.

The implant 10 has a coronary portion 12 sized to be received within the lumen of a coronary vessel such as the lumen 80 of a coronary artery 82 (FIGS. 12–13). The implant 10 has a myocardial portion 14 extending at about a right angle to the axis of coronary portion 12. The myocardial portion 14 is sized to extend from the coronary artery 82 directly through the myocardium 84 and into the left ventricle 86 of a patient's heart. The myocardial portion 14 is sized to have a length sufficient for the myocardial portion 14 to protrude into the left ventricle 86.

The coronary portion 12 has a first opening 16 and the myocardial portion 14 has a second opening 18 in communication with an interior 20 of the implant 10. Therefore, blood can freely flow through the implant 10 between the left ventricle 86 and the lumen 80 of the coronary artery 82. By way of non-limiting example, the implant 10 has a myocardial length ($L_M$) measured from coronary portion 12 to second opening 18 of about 25 mm. The implant 10 has a vessel length ($L_V$) measured from myocardial portion 14 to first opening 16 of about 6 mm.

As illustrated in FIGS. 1 and 2, a sleeve 22 surrounds the myocardial portion 14 and spaced from second opening 18. Preferably, the sleeve 22 is formed of a fabric having biocompatible fibers defining interstitial spaces to receive tissue growth. An example of such a fabric is polyethylene terephthalate (such as polyester fabric sold by DuPont Company under the trademark Dacron). Such a fabric permits rapid tissue integration into the fabric to anchor the fabric and, hence, the implant 10 to the patient's tissue.

The coronary portion 12 is secured in place by means of a reduced-diameter groove 24 formed adjacent the first end 16. With the reduced-diameter groove 24, a surgeon can place sutures 70 (FIG. 33) surrounding the coronary artery 82 to secure the coronary artery immobilized at the groove 24 as will be described.

The tool of the present invention is used in a procedure and in conjunction with tools as described in U.S. patent application Ser. No. 09/063,160. For ease of describing the tool and benefits of the present invention, certain of those tools and procedures are described herein with the novelty of the present invention over the aforementioned application being limited to a discussion of guide tool 600 and its use.

The procedure in which the present invention is used is illustrated in FIGS. 12–36. FIG. 12 is a plan view of an exterior surface 90 of a heart wall 84 with a coronary vessel 82 lying on the surface 90. A lumen 80 of the vessel 82 is shown in phantom lines. For ease of discussion, the procedure will be described with reference to vessel 82 being a coronary artery (e.g., LAD) on the left side of the heart overlying a left ventricle 86. Normal blood flow through the artery 82 is in the direction of arrow A.

Such blood flow is at least partially obstructed by an occlusion 88. FIG. 13 is a cross-sectional view of FIG. 12 showing the interior surface 92 of the heart wall (i.e., myocardium 84) and the left ventricle 86.

As taught in the '160 application, a surgeon places the distal tip 204 of guide needle 200 through the myocardium 84 at a location about 3.5 mm transverse to the axis of the artery 82 (FIGS. 14–15). When the side opening 210 of the needle 200 passes the inner surface 92 of the myocardium 84, blood flow through the needle 200 indicates the needle 200 has penetrated into the left ventricle 86. By observing external gradation marks (not shown in FIG. 14) on the needle 200, the surgeon can confirm the thickness of the myocardium 84 and select an implant 10 with a myocardial portion 14 of sufficient length to penetrate into the left ventricle 86 following completion of the procedure. The size of the artery 82 is observed to select an implant 10 of adequate diameter for the vessel portion 12 of the implant 10 to be placed in the artery 82.

Figure 36:
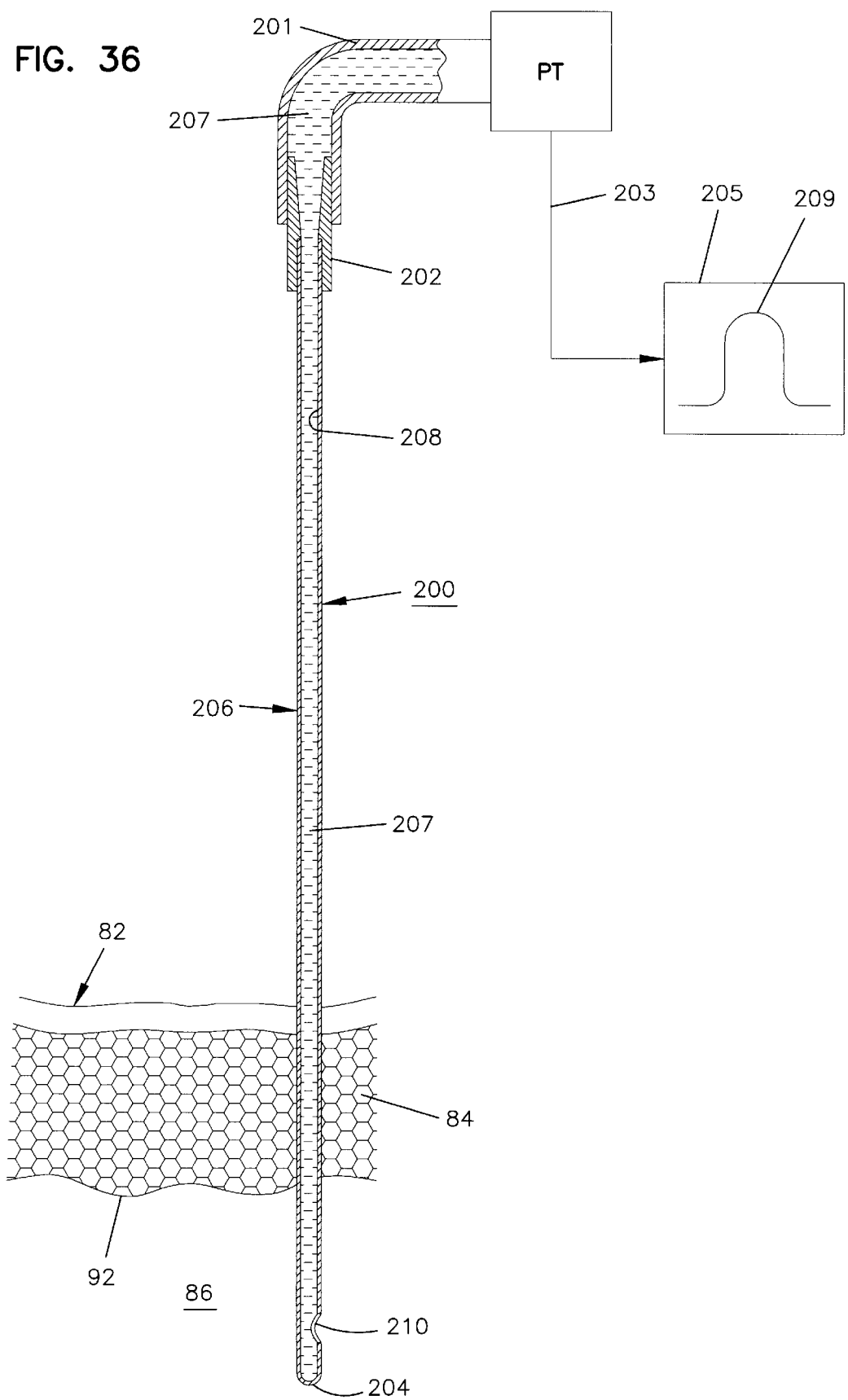
FIG. 36 is a side sectional schematic view showing an alternative procedure for measuring a myocardial thickness.

FIG. 36 illustrates an alternative tool and method for measuring myocardial thickness. In FIG. 36, the needle 200 is fitted with a hollow, flexible tube 201 at proximal end 202. An opposite end of the tube 201 is fitted to a pressure transducer PT. The pressure transducer PT is connected across a signal path 203 to a visual output 205 (such as a CRT). It will be appreciated that pressure transducers PT, visual outputs 205, signal paths 203 and connection of fluid filled tubes 201 to transducers PT are all well-known and hence shown schematically for purpose of ease of illustration.

The tube 201 and needle 200 are filled will a liquid 207 (preferably a saline solution). Since needle 200 is only open at opening 210, the liquid 207 is retained in the tube 201 and needle 200. When the needle 200 is passed through the myocardium 84, the opening 210 permits the liquid 207 to be subject to pressure variations in the left ventricle 86. The pressure variations are transferred by the liquid 207 to the pressure transducer PT. The pressure transducer PT generates a signal in response to the pressure variations and transmits the signal across path 203 to output 205. At output 205, a visual signal 209 is generated representing the pressure in the left ventricle 86 and advising the surgeon the opening 210 has penetrated into the left ventricle 86.

As will become apparent, the accurate placement of the guide needle 200 into the myocardium is important to axial alignment of the coronary portion 12 in the artery 82. If the angle of penetration of the needle 200 is too shallow, the coronary portion 12 will face downwardly toward the heart. If the angle of penetration of the needle 200 is too great, the coronary portion 12 will face upwardly away from the heart. The present invention is directed toward a guide tool 600 for placement of the needle 200 into the myocardium 84 at an angle to insure ultimate axial alignment of the coronary portion 12 with the coronary vessel 82.

Such a guide tool 600 is illustrated in FIGS. 3–6. The guide tool 600 is formed of one-piece, injected molded plastic. The guide tool 600 includes a base member 602 and a support member 604.

The base member 602 is generally straight and cylindrical with a diameter and length the same as the coronary portion 12 of the implant. The base member 602 has a lower base surface 602a for placement against an epicardial surface 84a (FIG. 7) of a heart adjacent the coronary vessel 82.

The base member 602 has a base axis $X_B$—$X_B$ determinable by the surgeon from visual inspection. The base axis $X_B$—$X_B$ permits placement of the base surface 602a on the epicardial surface 84a with the base axis $X_B$—$X_B$ parallel with an axis of the coronary vessel 82. Namely, with the base surface 602a flat on the epicardium 84a, the surgeon knows the base axis $X_B$—$X_B$ is not materially angled above or below (relative to the heart surface) the axis of the artery 82. Visual inspection permits the surgeon to ensure the base axis $X_B$—$X_B$ is not materially angled transversely relative to the vessel axis.

The support member 604 supports a myocardial penetrator which in a preferred embodiment is the guide needle 200 but could be any device used to form a hole through the myocardium 84. The support member 604 supports the guide needle 200 for movement along a support axis $X_S$—$X_S$ in a line of travel parallel to the support axis $X_S$—$X_S$ and substantially restricting the myocardial guide needle 200 from movement transverse to the support axis $X_S$—$X_S$. A hole 605 extends completely through the support member 604. The hole 605 is slightly smaller than the diameter of the guide needle 200 so that the needle 200 can still be urged through the hole 605 but is held fixed to the support member 604 by friction when a surgeon stops urging the needle 200 through the hole 605.

The support member 604 is secured to the base member 602 with the support axis $X_S$—$X_S$ and base axis $X_B$—$X_B$ defining a support angle B. The support angle B and the implant angle $B_I$ are supplementary angles (i.e., total 180°). In the preferred embodiment where the implant myocardial portion 14 is set at 90° to the coronary portion 12, both the support angle B and implant angle $B_I$ are 90°.

A gusset 606 connects the support member 604 and base member 602. In addition to maintaining fixed relative positioning between the base and support members 602, 604, the gusset 606 is a convenient handle which a surgeon can grasp with a tool (e.g., forceps) to manipulate the guide tool 600.

As shown in FIGS. 7–11, the guide needle 200 has a marking 220 at a fixed distance from the opening 210. The support member 604 has an open slot 610 to permit observation of a position of the marking 220 as the guide needle 200 moves in the guide tool 600. Markers 611–614 spaced along the length of the support member 604 cooperate with the guide needle marking 220 to indicate a distance of the opening 210 from the base surface 602a.

Figure 7:
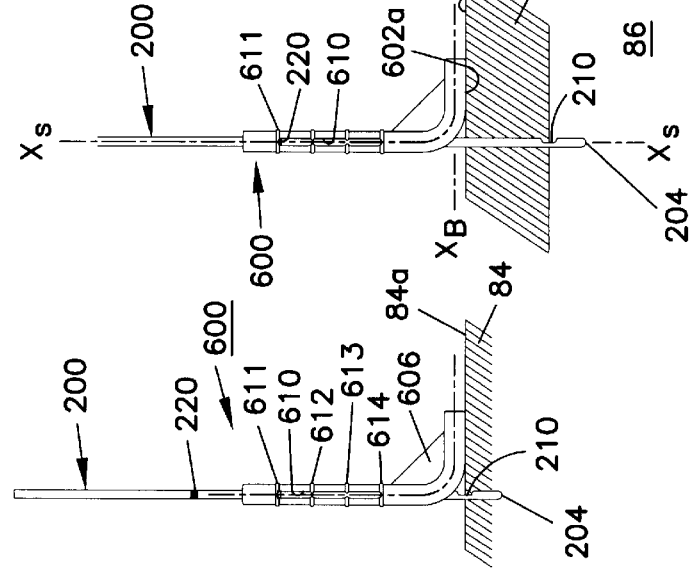
FIG. 7 is a side elevation view of a guide needle within the guide tool and with the tool on a heart surface and with an opening of the needle at the heart surface.
Figure 8:
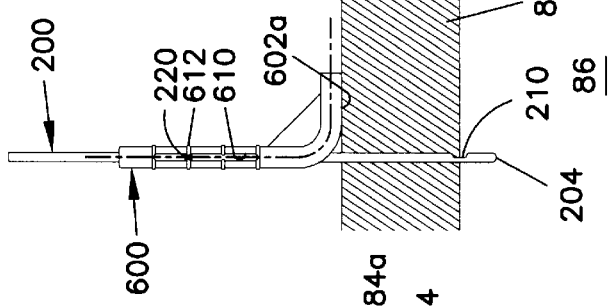
FIG. 8 is the view of FIG. 7 with the needle penetrated through a myocardium having a thickness such that a fixed marking on the needle aligns with a first marker of the guide tool when the needle opening is at an interior surface of the heart wall.
Figure 9:
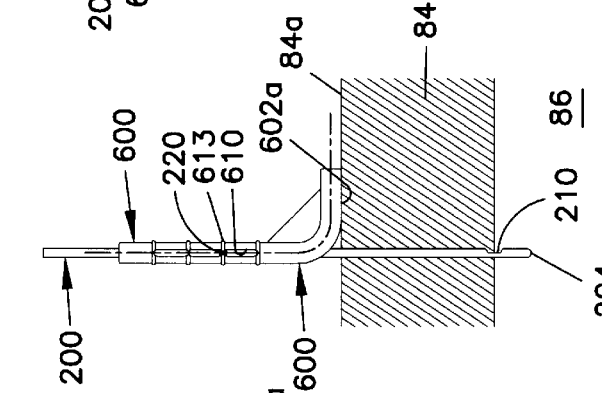
FIG. 9 is the view of FIG. 7 with the needle penetrated through a myocardium having a thickness such that a fixed marking on the needle aligns with a second marker of the guide tool when the needle opening is at an interior surface of the heart wall.
Figure 10:
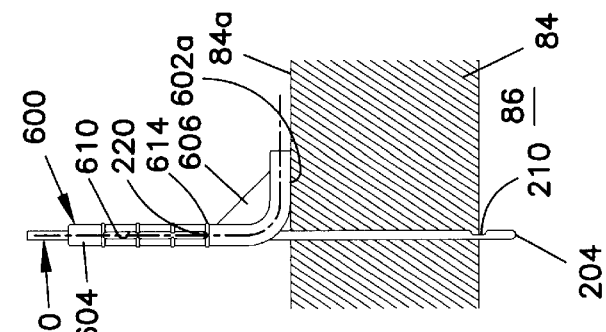
FIG. 10 is the view of FIG. 7 with the needle penetrated through a myocardium having a thickness such that a fixed marking on the needle aligns with a third marker of the guide tool when the needle opening is at an interior surface of the heart wall.
Figure 11:
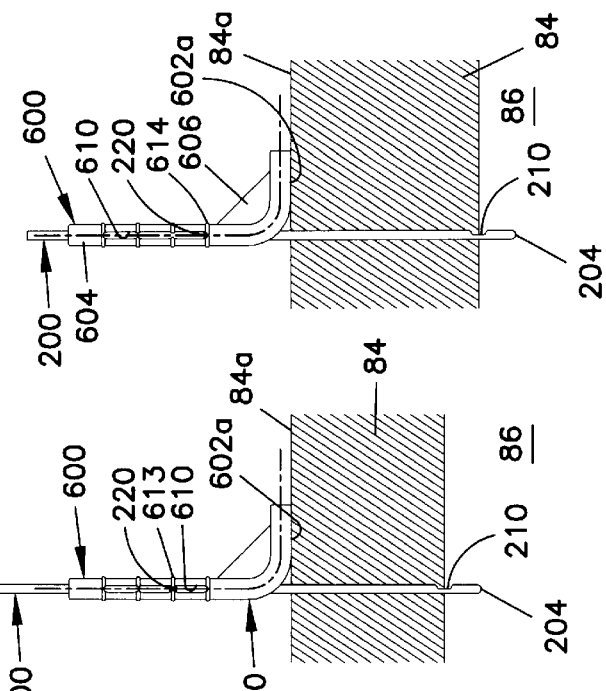
FIG. 11 is the view of FIG. 7 with the needle penetrated through a myocardium having a thickness such that a fixed marking on the needle aligns with a fourth marker of the guide tool when the needle opening is at an interior surface of the heart wall.

FIG. 7 illustrates use of the guide tool 600 with the needle 200 positioned with the opening 210 in line with the base surface 602a (i.e., at the epicardial surface). FIGS. 7–11 illustrate use of the guide tool 600 with the needle 200 positioned such that the opening 210 has penetrated into the left ventricle through myocardium of varying thickness to show how the thickness can be gauged by positioning of the needle marking 220 relative to the support markings 611–614. Preferably, implants 10 will be available in sizes corresponding with the depths indicated by the markings 611–614. Therefore, a surgeon can use the tool 600 to select an appropriately sized implant 10.

Having described the present invention, its benefits will now become apparent with a description of a remainder of a procedure as more fully described in the aforementioned '160 application.

A guide wire 100 is passed through the needle 200. (FIGS. 16–17 in which the guide tool 600 is not shown). The guide needle 200 and guide tool 600 are then removed over the guide wire 100 leaving only the guide wire 100 extending through the thickness of the myocardium 84 (FIGS. 18–19). At this point, the use of the guide tool 600 of the present invention is complete. However, the benefits are recognized with the placement of the implant in the coronary artery. Therefore, a brief description of the remainder of the procedure is now given to complete an understanding of the benefits of the present invention. The remaining procedures and tools are more fully described in U.S. patent application Ser. No. 09/063,160.

With the guide wire 100 insuring desired positioning, a combined myocardial sheath 300 and dilator 400 are passed over the wire 100 and are urged through the myocardium 84 (FIGS. 20–22). A combined myocardial sheath 300 and dilator 400 urge the tissue of the myocardium 84 apart to form an opening through the myocardium 84 sufficient to pass the myocardial portion 14 of the implant 10. The stiff dilator 400 prevents deformation of the myocardial sheath 300. The dilator 400 and guide wire 100 are removed leaving only the myocardial sheath 300 extending through the myocardium 84 (FIGS. 23–24).

The myocardial portion 14 of the implant 10 is placed within the myocardial sheath 300 (FIGS. 25–26). The outside diameter of the fabric sleeve 22 closely matches the internal diameter of the sheath body 302.

The artery 82 is ligated with sutures 72 distal to the obstruction 88 and transversely incised at an incision 74 distal to the ligation (FIG. 27). The incision 74 separates the artery 82 into a proximal portion 82a and a distal portion 82b. The distal portion 82b presents an arterial opening 83 at the incision 74.

In the figures, the incision 74 is shown extending transverse to the artery 82 and completely through the artery 82. Such an incision 74 is shown for ease of illustration. In practice, the surgeon may elect to form incision 74 only partly through (e.g., 50%) the artery 82 and further forming a longitudinal incision on the top of the distal portion 82b of the artery 82 to provide a flap-opening to the distal portion 82b of the artery 82.

A leading end 510 of a vessel sheath 500 is placed within the incised opening 83 of the distal portion 82b of the artery 82 (FIG. 28). Due to the taper 508 of the vessel sheath 500, the vessel sheath 500 can be placed in a small diameter artery 82 and urged into the artery 82 with the artery 82 dilated over a cylindrical body 506 of the vessel sheath 500 (FIGS. 29–30).

With the vessel sheath 500 fully inserted into the artery 82, the implant 10 and myocardial sheath 300 can be manipulated to align the open end 16 of the coronary portion 12 of the implant 10 with an open trailing end 512 of the vessel sheath 500. Since the myocardium 84 is a pliable tissue, the implant 10 and myocardial sheath 300 can easily be manipulated (such as tilted) to effect such alignment (FIG. 31).

The open end 16 of the coronary portion 12 of the implant 10 is passed through the open trailing end 512 of the vessel sheath 500. The vessel portion 12 is advanced into the vessel sheath body 502 at least as far as the start of the tapered portion 508 of the vessel sheath 500 (FIG. 32).

The artery 82 is secured to the vessel portion 12 of the implant by sutures 70 surrounding the artery 82 in overlying relation to the groove 24 (FIG. 33). The surgeon grasps the handle 504 of the vessel sheath 500 and pulls the sheath body 502 over the implant 10. The vessel sheath body 502 splits open at a part-line and the wall of the vessel sheath body 502 flexes open to permit the sheath body 502 to clear the implant 10 leaving only the vessel portion 12 of the implant 10 within the artery 82. Sutures 70 are placed following removal of the vessel sheath 500. The removal of the vessel sheath body 502 further acts to draw the artery 82 over the vessel portion 12 of the implant 10.

The surgeon grasps the handle 306 of the myocardial sheath 300 and pulls the sheath 300 out of the myocardium 84 (FIGS. 34–35). The myocardial sheath 300 splits open at a part-line and the wall of the myocardial sheath 300 flexes open to permit the sheath 300 to clear the implant 10 leaving only the myocardial portion 14 and sleeve 22 of the implant 10 within the myocardium 84. Since the myocardial portion 14 is placed in a hole in the myocardium 84 formed by the dilator 400, the tissue of the myocardium 84 is biased to urge against the implant 10 holding it in place. Subsequent tissue growth into the sleeve 22 further secures the implant 10 within the myocardium.

In the foregoing description, the invention has been shown in a preferred embodiment. Modifications and equivalents of the disclosed concepts are intended to be included within the scope of the claims.

What is claimed is:

1. An apparatus for controlling a direction of formation of a hole through a myocardium for subsequent placement into said hole of a myocardial portion of a transmyocardial implant where the implant also includes a coronary portion having a coronary axis set at an implant angle to a myocardial axis of the myocardial portion, the apparatus comprising:

A. a narrow, elongated base member having
 a. a base surface for placement against an epicardial surface of a heart adjacent a coronary vessel having a vessel axis;
 b. a determinable base axis extending parallel to a longitudinal axis of said base member for placement of the base surface on the epicardial surface with the base axis parallel with the vessel axis by placement of said base member on said epicardial surface adjacent to said vessel;

B. a straight and rigid myocardial penetrator;

C. a support member for supporting the straight and rigid myocardial penetrator for movement along a straight support axis in a line of travel parallel to the support axis and substantially restricting the myocardial penetrator from movement transverse to the support axis;

D. the support member secured to the base member with the support axis and base axis defining a support angle and with said base member extending from a side of said support member for said support member and base member to define a substantially L-shaped configuration; and E. the support angle and the implant angle being supplementary angles.

2. An apparatus according to claim 1 wherein the support member includes a bore to receive the myocardial penetrator and a radial opening through the support member to reveal a portion of said myocardial penetrator within said support member.

3. An apparatus according to claim 2 wherein the support member includes an indicator at said opening.

4. An apparatus according to claim 1 wherein the base member has a length substantially equal to a length of said coronary portion of said implant.

* * * * *